United States Patent [19]

Noda et al.

[11] Patent Number: 4,995,997

[45] Date of Patent: Feb. 26, 1991

[54] ANTIBACTERIAL WATER-SOLUBLE CUTTING FLUID RESISTANT TO YEAST-LIKE FUNGI

[75] Inventors: Masahiro Noda; Masaharu Fuchigami; Akira Akagawa, all of Kanagawa, Japan

[73] Assignee: Yushiro Chemical Industry Co., Ltd., Japan

[21] Appl. No.: 479,570

[22] Filed: Feb. 14, 1990

[30] Foreign Application Priority Data

Mar. 16, 1989 [JP] Japan .................................. 1-62288

[51] Int. Cl.$^5$ .......................................... C10M 173/02
[52] U.S. Cl. .................................... 252/49.5; 252/50; 252/51.5 A
[58] Field of Search ..................... 252/49.5, 50, 51.5 A

[56] References Cited

U.S. PATENT DOCUMENTS

| | | | |
|---|---|---|---|
| 4,116,874 | 9/1978 | Sugiura et al. ......................... | 252/50 |
| 4,206,229 | 6/1980 | Brandman et al. ................. | 252/49.5 |
| 4,212,750 | 7/1980 | Gorman ............................... | 252/49.5 |
| 4,217,363 | 8/1980 | Brandman et al. ................. | 252/49.5 |
| 4,269,720 | 5/1981 | Bartleson et al. ..................... | 252/50 |
| 4,749,503 | 7/1988 | Bennett et al. ..................... | 252/49.5 |
| 4,778,614 | 10/1988 | Rawlenson et al. ............... | 252/49.3 |
| 4,801,362 | 1/1989 | Fenyes ............................... | 252/49.3 |

FOREIGN PATENT DOCUMENTS 61-40720  9/1986  Japan.
63-4880   1/1988  Japan.

*Primary Examiner*—Jacqueline V. Howard
*Attorney, Agent, or Firm*—Lowe, Price, Leblanc, Becker & Shur

[57] ABSTRACT

A bactericide is added to conventional water-soluble cutting fluids to suppress deterioration by microorganisms. Such fluids are however accompanied by the drawbacks that the bactericide has a narrow antibacterial spectrum and moreover its effects last a short time. It is the object of the present invention to offers water-soluble cutting fluids which remain resistant to a wide variety of microorganisms for a long time. The present invention therefore offers water-soluble cutting fluids to which has been added a specific amine selected from amines known to date.

4 Claims, No Drawings

ANTIBACTERIAL WATER-SOLUBLE CUTTING FLUID RESISTANT TO YEAST-LIKE FUNGI

BACKGROUND OF THE INVENTION (a) Field of the Invention:

The present invention relates to water-soluble cutting fluids useful for cutting or grinding work, and more specifically to water-soluble cutting fluids featuring suppressed deterioration by microorganisms. Still more specifically, the present invention is concerned with water-soluble cutting fluids resistant to yeast-like fungi. The term "water-soluble" as used herein should be interpreted in a broad sense as commonly accepted in the present field of art, so that it can be taken as an equivalent to "water-miscible" and can embrace "water-dispersible" therein.

(b) Description of the Related Art:

Water-soluble cutting fluids useful for cutting or grinding metal contain, as components, a mineral oil, a fatty oil, an extreme-pressure additive, a surfactant, a defoaming agent, a metal anticorrosive, an antiseptic, a fungicide, and the like. These components are mixed at a ratio suitable to the end use. For use, such water-soluble cutting fluids are generally diluted 10–100 fold with water. The thus-diluted solutions are called "coolants".

A coolant is required to exhibit good performance not only in cutting or grinding performance (i.e., primary performance) but also in working efficiency and the like (i.e., secondary performance). Secondary performance requirements include good rust resistance, slow deterioration and easy maintenance, harmlessness to the human body, low foaming tendency, etc.

Among these secondary aspects, it is a very important to avoid deterioration by microorganisms for the following reasons. If putrefaction of a coolant develops due to deterioration by microorganisms, both first performance and second performance capabilities are reduced and moreover, the working environment is deteriorated by an unpleasant odor. Further, growth of fungi in the coolant may lead not only to lowered first and second performances but also pipe clogging in a recirculation system.

As a method for preventing deterioration of such water-soluble cutting fluids by microorganisms, it has heretofore been the practice to add a bactericide.

However, such a bactericide may exhibit good activities against certain specific microorganisms but may not be effective against another type or other types of microorganisms, resulting in the problem that the breadth of applicability is restricted. Moreover, there is another problem in that the bactericide may decompose or otherwise become inactive in a short time, so that long-term bactericidal effects are extremely poor. In addition, the use of the bactericide at a high concentration results in the problem that it gives adverse effects to the human body, especially severe skin irritation which may induce skin roughness or chapping, dermatitis, etc. When a bactericide is used, care must always be exercised to maintain constant concentration, leading to a further problem of increased manpower and cost.

Incidentally, the invention disclosed in Japanese Patent Publication No. 40720/1986 features the addition of a diamine represented by the below-described formula to a water-soluble cutting fluid whereby the tendency of deterioration of the water-soluble cutting fluid by microorganisms can be improved:

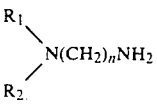

wherein $R_1$ means a hydrogen atom or an alkyl, alkenyl, cycloalkyl, alkylaryl, aralkyl or aryl group having up to 24 carbon atoms, $R_2$ denotes an alkyl, alkenyl, cycloalkyl, alkylaryl or aryl group having up to 24 carbon atoms, and n stands for an integer of 4–18.

Examples of the diamine, which are disclosed in the patent publication, include dibutylaminododecylamine, ethylaminoethylamine, di-2-propenylaminoethylamine, cyclohexylaminoethylamine, 3,5-dimethylphenylaminobutylamine, benzylaminooctylamine and phenylaminobutylamine.

Further, the invention disclosed in Japanese Patent Publication No. 4880/1988 resides in the addition of an amine represented by the below-described formula to a water-soluble cutting fluid so that the tendency of the water-soluble cutting fluid to deteriorate through corruption by microorganisms can be reduced:

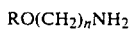

wherein R means an alkyl, alkenyl, cycloalkyl, alkylaryl, aralkyl or aryl group having up to 24 carbon atoms, and n stands for an integer of 2–18. Exemplary amines in this prior art publication include 2-ethylhexyloxypropylamine, lauryloxyethylamine, 2-ethylhexyloxydodecylamine, lauryloxydibutylamine, cyclohexyloxypropylamine and benzyloxypropylamine.

The amines proposed in the above patent publications are effective against a wide variety of bacteria and fungi. However, their bacterial activities against yeast-like fungi are weak. The current situation is therefore that they cannot bring about satisfactory effects against the deterioration of water-soluble cutting fluids caused by yeast-like fungus or fungi.

SUMMARY OF THE INVENTION

An object of the present invention is to solve such problems as referred to hereinabove and to provide a water-soluble cutting fluid having antibacterial activities even against yeast-like fungi so that it has excellent resistance to the deterioration by microorganisms.

The present inventors have now found that the addition of a specific amine or amine derivative, which will be described in detail hereinbelow, to a conventional water-soluble cutting fluid can provide a water-soluble cutting fluid having extremely good antibacterial activities against a wide variety of microorganisms including yeast-like fungi.

In one aspect of the present invention, there is thus provided an antimicrobial water-soluble cutting fluid comprising a mineral oil and/or fatty oil, an extreme-pressure additive and a surfactant, wherein said fluid further comprises an amine or amine derivative represented by the following formula (I):

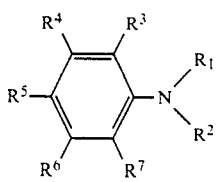  (I)

or by the following (II):

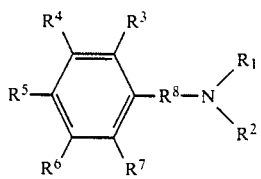  (II)

wherein $R^1$ through $R^7$ individually mean a hydrogen atom, a substituted or unsubstituted alkyl, alkenyl, cycloalkyl, alkylaryl, aralkyl, aryl, hydroxyalkyl or alkoxyl group, or a nitrogen-containing heterocyclic group having up to 10 carbon atoms, $R^1$ and $R^2$ may be coupled together into a nitrogen-containing heterocyclic group along with the nitrogen atom to which $R^1$ and $R^2$ are bonded, or $R^3$ through $R^7$ individually mean a hydroxyl, amino, substituted amino, aminocarbonyl or aliphatic acyl group, and $R^8$ denotes an alkylene group having 1-4 carbon atoms.

Most preferably, the alkyl, alkenyl, cycloalkyl, alkylaryl, aralkyl, aryl, hydroxyalkyl and alkoxyl groups represented by $R^1$ to $R^7$ in the above formulae (I) and (II) have up to 7 carbon atoms.

The antimicrobial water-soluble cutting fluid according to the present invention is far superior to conventional water-soluble cutting fluids in its resistance to deterioration caused by yeast-like fungi and other microorganisms, thereby making it possible to prevent the occurrence of any putrefactive odor during use over a prolonged period of time. The use of any one of the water-soluble cutting fluids of the present invention therefore permits saving of cutting fluid and a reduction in the running cost.

DETAILED DESCRIPTION OF THE INVENTION AND PREFERRED EMBODIMENTS (Amines)

Amines usable in the practice of the present invention include anilinoamines, namely, the compounds represented by the formula (I) and aralkylamines, namely, the amines represented by the formula (II).

(Anilinoamines)

The anilinoamines usable in the practice of the present invention, namely, the compound represented by the formula (I) include the following compounds:

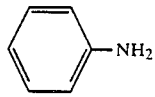

Aniline

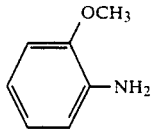

o-Anisidine

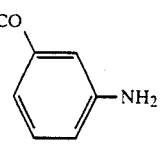

m-Anisidine

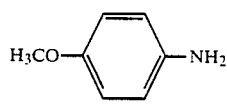

p-Anisidine

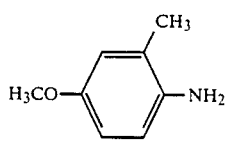

4-Methoxy-2-methylaniline

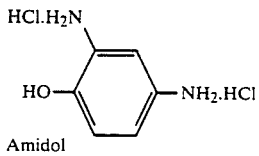

Amidol

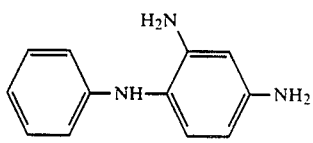

4-Anilino-m-phenylenediamine

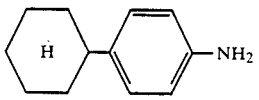

4-Cyclohexylaniline

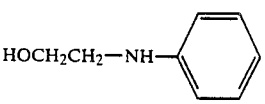

2-Anilinoethanol

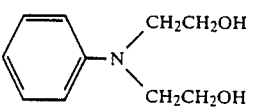

2-Anilinodiethanol

-continued

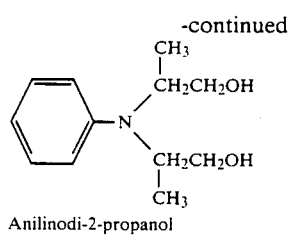

Anilinodi-2-propanol

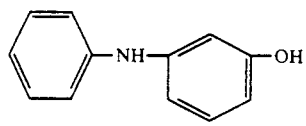

m-Anilinophenol

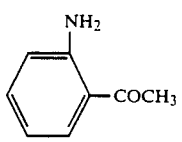

2-Aminoacetophenone

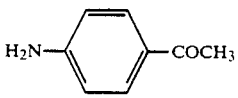

4-Aminoacetophenone

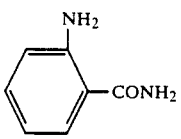

2-Aminobenzaminde

4-Aminobenzamide

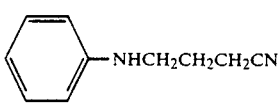

3-Anilinopropionitrile

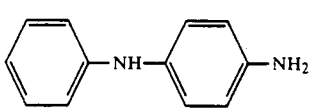

N-Phenyl-p-phenylenediamine

Among these anilinoamines, the following compounds are most preferred:
4-Methoxy-2-methylaniline;
4-Anilino-m-phenylenediamine;
4-Cyclohexylaniline;
m-Anilinophenol;
2-Aminoacetophenone;
4-Aminoacetophenone; and
N-Phenyl-p-phenylenediamine.

(Aralkylamines)

The aralkylamines usable in the practice of the present invention, namely, the compounds represented by the formula (II) include the following compounds:

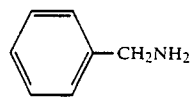

Benzylamine

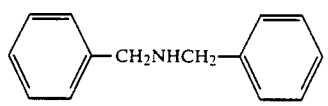

Dibenzylamine

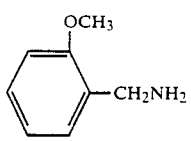

o-Methoxybenzylamine

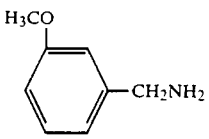

m-Methoxybenzylamine

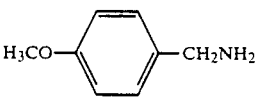

p-Methoxybenyzlamine

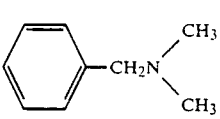

N,N-Dimethylbenzylamine

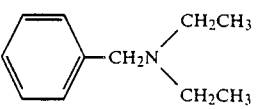

N,N-Diethylbenzylamine

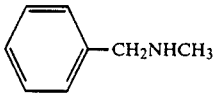

N-Methylbenzylamine

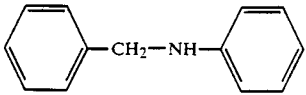

N-Phenylbenzylamine

-continued

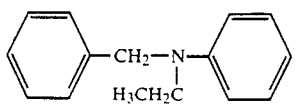

N-Phenyl-N-ethylbenzylamine

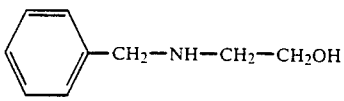

N-(2-Hydroxyethyl)benzylamine

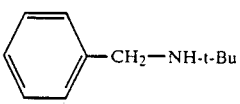

N-(t-Butyl)benzylamine

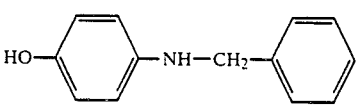

p-Benzylaminophenol

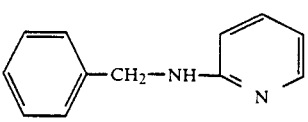

2-Benzylaminopyridine

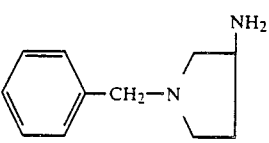

1-Benzyl-3-aminopyrrolidine

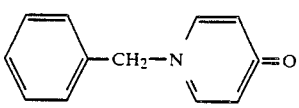

N-Benzyl-4-piperidone

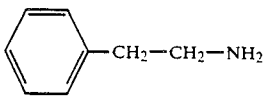

2-Phenylethylamine

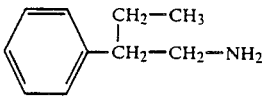

2-Phenylbutylamine

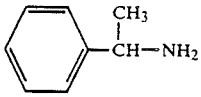

d,l-α-Methylbenzylamine

-continued

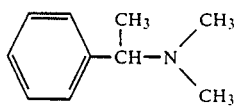

N,N-Dimethyl-d,l-α-methyl-benzylamine

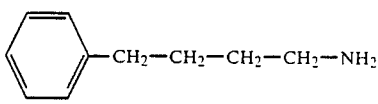

4-Phenylbutylamine

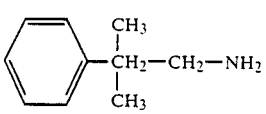

2-Phenyl-t-butylamine

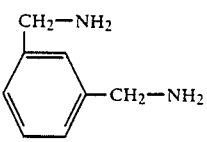

m-Xylenediamine

Among these aralkylamines, the following compounds are most preferred:
N,N-Diethylbenzylamine;
N-Phenylbenzylamine;
N-Phenyl-N-ethylbenzylamine;
N-(t-butyl)benzylamine;
2-Phenylethylamine;
N,N-Dimethyl-d,l-α-methylbenzylamine; and
2-Phenyl-t-butylamine.

(Amine Concentration in Coolant)

In the present invention, the concentration of each of the above-described amines in coolants may desirably be 0.001–1 wt. %, preferably 0.01–0.5 wt. %, and most preferably 0.03–0.5 wt. %. Concentrations lower than 0.001 wt. % are too little to effectively prevent deterioration by microorganisms. On the other hand, the ability to prevent degradation by microorganisms is not improved even when the amine concentration in coolants exceeds 1 wt. %. It is hence economically disadvantageous to incorporate the amines at such an unduly high concentration.

These amines can exhibit similar effects no matter whether they are added to the stock fluids of water-soluble cutting fluids or to coolants.

(Preparation Procedure)

To prepare a water-soluble cutting fluid according to the present invention, it is only necessary to mix one or more of the above-described amines with the components of a conventional water-soluble cutting fluid in a manner known per se in the art. Components such as mineral oil, fatty oil, extreme pressure additive, surfactant, defoaming agent, metal rust preventive and antioxidant can be chosen as needed for use in the present invention from those employed to date.

The present invention will next be described in detail by the following examples. It should however be borne in mind that this invention is by no means limited to or by the examples.

Table 1 shows the compositions of certain water-soluble cutting fluids of the emulsion type, while Table 2 describes those of the soluble type. In each of these tables, the figures pertaining to the compositions are all by wt. %.

TABLE 1-1

|  | Example | | | | | |
| --- | --- | --- | --- | --- | --- | --- |
|  | 1 | 2 | 3 | 4 | 5 | 6 |
| Mineral oil | 72 | 56 | 59 | 53 | 51 | 57 |
| Chlorinated paraffin | — | — | — | 9 | 10 | 15 |
| Fatty oil | — | 15 | 15 | 10 | 10 | — |
| Anionic surfactant | 19 | 20 | 19 | 19 | 19 | 21 |
| Nonionic surfactant | 7 | 7 | 5 | 7 | 6 | 5 |
| 4-Methoxy-2-methylaniline | 2 | — | — | — | — | — |
| 4-Cyclohexylaniline | — | 2 | — | — | — | — |
| 4-Anilino-m-phenyldiamine | — | — | 2 | — | — | — |
| m-Anilinophenol | — | — | — | 2 | — | — |
| N,N-Dimethylbenzylamine | — | — | — | — | 2 | — |
| N-phenylbenzylamine | — | — | — | — | — | 2 |

TABLE 1-2

|  | Example | | | Comp. Ex. | | |
| --- | --- | --- | --- | --- | --- | --- |
|  | 7 | 8 | 9 | 1 | 2 | 3 |
| Mineral oil | 53 | 54 | 71 | 73 | 58 | 55 |
| Chlorinated paraffin | — | 9 | — | — | — | 9 |
| Fatty oil | 19 | 10 | — | — | 15 | 10 |
| Anionic surfactant | 21 | 19 | 20 | 19 | 19 | 19 |
| Nonionic surfactant | 5 | 6 | 5 | 7 | 7 | 7 |
| p-Benzylaminophenol | 2 | — | — | — | — | — |
| d,l-α-Methylbenzylamine | — | 2 | — | — | — | — |
| 4-Phenylbutylamine | — | — | 2 | — | — | — |
| Commercial antiseptic (triazine type) | — | — | — | 1 | — | — |
| Commercial antiseptic (thiazoline type) | — | — | — | — | 1 | — |

TABLE 2-1

|  | Example | | | | |
| --- | --- | --- | --- | --- | --- |
|  | 10 | 11 | 12 | 13 | 14 |
| Anionic surfactant | 41 | 45 | 47 | 45 | 45 |
| Nonionic surfactant | 27 | 23 | 21 | 23 | 23 |
| Amidol | 2 | — | — | — | — |
| 2-Anilinodiethanol | — | 2 | — | — | — |
| 3-Ailinopropionitrile | — | — | 2 | — | — |
| N-Phenyl-p-phenylenediamine | — | — | — | 2 | — |
| N-(2-Hydroxyethyl)benzylamine | — | — | — | — | 2 |
| Water | 30 | 30 | 30 | 30 | 30 |

TABLE 2-2

|  | Example | | Comp. Ex. | | |
| --- | --- | --- | --- | --- | --- |
|  | 15 | 16 | 4 | 5 | 6 |
| Anionic surfactant | 45 | 45 | 46 | 46 | 47 |
| Nonionic surfactant | 23 | 23 | 23 | 23 | 23 |
| 1-Benzyl-3-aminopyrrolidine | 2 | — | — | — | — |
| N-Benzyl-4-piperidone | — | 2 | — | — | — |
| Commercial antiseptic (triazine type) | — | — | 1 | — | — |
| Commercial antiseptic (thiazoline type) | — | — | — | 1 | — |
| Water | 30 | 30 | 30 | 30 | 30 |

(Evaluation of Performance)

The following experiments were conducted on the water-soluble cutting fluids whose compositions are shown in Table 1 and Table 2, respectively to evaluate their performance.

(1) Preparation of samples

Samples were prepared by separately diluting the water-soluble cutting fluids of Table 1 and those of Table 2 with sterilized water to a concentration of 3 wt. % (Table 1) or 2 wt. % (Table 2) and also diluting the water-soluble cutting fluids of the comparative examples with sterilized water.

(2) Deterioration tests by microorganisms

Each sample solution (400 ml) was placed in a sterilized 500-ml flat bottom flask. At the intervals of the 1st, 2nd, 4th, 8th, 13th and 17th days after the initiation of the test, the sample solution was inoculated with 1 wt. % portions of a putrefied emulsion as a seed culture (viable cell count: $2 \times 10^8$ cells/ml; mold cell count: $1 \times 10^4$ cells/ml; yeast-like fungus count: $1 \times 10^4$ cells/ml) while being subjected to shaking culture at 200 rpm and 30° C. for 21 days. On the 0th, 3rd, 7th, 14th and 21st days after the initiation of the test, portions of the sample solution were sterilely collected, respectively. Viable cells, mold cells and yeast-like fungi cells in each portion of the sample solution were counted. At the same time, measurement of its pH and determination of the presence or absence of any unpleasant odor were also conducted.

(Evaluated Items)

(1) pH pH was measured by a glass electrode pH meter. A decrease in pH indicates the degree of deterioration by microorganisms. A lower pH is considered to indicate a higher progress of deterioration by microorganisms.

(2) Measurement of viable cell counts and fungus cell counts

Each viable cell count was measured by the plate count technique, using an ordinary agar medium.

Each mold cell count and each yeast-like fungus count were determined by the plate count technique, using potato-dextrose-agar medium added with antibiotics (chloramphenicol and tetracycline) and Sabouraud agar medium added with tetracycline, respectively.

(3) Ranking of unpleasant odor

Unpleasant odor was ranked in accordance with the following 3-stage system:

A: No putrefactive odor.
B: Some putrefactive odor.
C: Strong putrefactive odor.

The measurement results along the passage of days are summarized in Table 3 and Table 4:

TABLE 3-1

| Sample | Item tested | Days passed | | |
| --- | --- | --- | --- | --- |
|  |  | 0 | 3 | 7 |
| Ex. 1 | pH | 9.2 | 9.2 | 9.1 |
|  | Viable cell count (cells/ml) | 0 | $<10^3$ | $<10^3$ |
|  | Mold cell count (cells/ml) | 0 | $<10$ | $<10$ |
|  | Yeast-like fungus cell count (cells/ml) | 0 | $<10$ | $<10$ |
|  | Unpleasant odor | A | A | A |
| Ex. 2 | pH | 9.1 | 9.1 | 9.0 |
|  | Viable cell count (cells/ml) | 0 | $<10^3$ | $<10^3$ |
|  | Mold cell count (cells/ml) | 0 | $<10$ | $<10$ |
|  | Yeast-like fungus cell count (cells/ml) | 0 | $<10$ | $<10$ |
|  | Unpleasant odor | A | A | A |
| Ex. 3 | pH | 9.3 | 9.2 | 9.1 |
|  | Viable cell count (cells/ml) | 0 | $<10^3$ | $<10^3$ |
|  | Mold cell count (cells/ml) | 0 | $<10$ | $<10$ |
|  | Yeast-like fungus cell count (cells/ml) | 0 | $<10$ | $<10$ |
|  | Unpleasant odor | A | A | A |
| Ex. 4 | pH | 9.3 | 9.2 | 9.1 |
|  | Viable cell count (cells/ml) | 0 | $<10^3$ | $<10^3$ |
|  | Mold cell count (cells/ml) | 0 | $<10$ | $<10$ |

TABLE 3-1-continued

| Sample | Item tested | Days passed 0 | Days passed 3 | Days passed 7 |
|---|---|---|---|---|
| | Yeast-like fungus cell count (cells/ml) | 0 | <10 | <10 |
| | Unpleasant odor | A | A | A |
| Ex. 5 | pH | 9.3 | 9.2 | 9.1 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |
| | Unpleasant odor | A | A | A |
| Ex. 6 | pH | 9.2 | 9.2 | 9.1 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |
| | Unpleasant odor | A | A | A |
| Ex. 7 | pH | 9.2 | 9.1 | 9.0 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |
| | Unpleasant odor | A | A | A |
| Ex. 8 | pH | 9.3 | 9.2 | 9.2 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |
| | Unpleasant odor | A | A | A |
| Ex. 9 | pH | 9.2 | 9.1 | 9.0 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |
| | Unpleasant odor | A | A | A |
| Comp. Ex. 1 | pH | 9.0 | 8.9 | 8.8 |
| | Viable cell count (cells/ml) | 0 | <$10^3$ | <$10^3$ |
| | Mold cell count (cells/ml) | 0 | <10 | 20 |
| | Yeast-like fungus cell count (cells/ml) | 0 | 24 | $1 \times 10^2$ |
| | Unpleasant odor | A | B | C |
| Comp. Ex. 2 | pH | 9.0 | 8.9 | 8.8 |
| | Viable cell count (cells/ml) | 0 | <$10^3$ | <$10^3$ |
| | Mold cell count (cells/ml) | 0 | <10 | 18 |
| | Yeast-like fungus cell count (cells/ml) | 0 | 14 | 41 |
| | Unpleasant odor | A | B | C |
| Comp. Ex. 3 | pH | 9.0 | 8.8 | 8.6 |
| | Viable cell count (cells/ml) | 0 | $3 \times 10^3$ | $4 \times 10^4$ |
| | Mold cell count (cells/ml) | 0 | $2 \times 10^2$ | $3 \times 10^2$ |
| | Yeast-like fungus cell count (cells/ml) | 0 | $2 \times 10^2$ | $5 \times 10^3$ |
| | Unpleasant odor | A | C | C |

TABLE 3-2

| Sample | Item tested | Days passed 14 | Days passed 21 |
|---|---|---|---|
| Ex. 1 | pH | 9.0 | 8.9 |
| | Viable cell count (cells/ml) | <$10^3$ | $3 \times 10^3$ |
| | Mold cell count (cells/ml) | <10 | <10 |
| | Yeast-like fungus cell count (cells/ml) | <10 | <10 |
| | Unpleasant odor | A | A |
| Ex. 2 | pH | 8.9 | 8.8 |
| | Viable cell count (cells/ml) | $1 \times 10^3$ | $4 \times 10^3$ |
| | Mold cell count (cells/ml) | <10 | <10 |
| | Yeast-like fungus cell count (cells/ml) | <10 | <10 |
| | Unpleasant odor | A | A |
| Ex. 3 | pH | 9.0 | 8.9 |
| | Viable cell count (cells/ml) | <$10^3$ | <$10^3$ |
| | Mold cell count (cells/ml) | <10 | <10 |
| | Yeast-like fungus cell count (cells/ml) | <10 | <10 |
| | Unpleasant odor | A | A |
| Ex. 4 | pH | 9.0 | 8.9 |
| | Viable cell count (cells/ml) | <$10^3$ | $2 \times 10^3$ |
| | Mold cell count (cells/ml) | <10 | <10 |
| | Yeast-like fungus cell count (cells/ml) | <10 | <10 |
| | Unpleasant odor | A | A |
| Ex. 5 | pH | 9.0 | 9.0 |
| | Viable cell count (cells/ml) | <$10^3$ | <$10^3$ |
| | Mold cell count (cells/ml) | <10 | <10 |
| | Yeast-like fungus cell count (cells/ml) | <10 | <10 |
| | Unpleasant odor | A | A |
| Ex. 6 | pH | 9.0 | 8.9 |
| | Viable cell count (cells/ml) | <$10^3$ | $1 \times 10^3$ |
| | Mold cell count (cells/ml) | <10 | <10 |
| | Yeast-like fungus cell count (cells/ml) | <10 | <10 |
| | Unpleasant odor | A | A |
| Ex. 7 | pH | 9.0 | 8.9 |
| | Viable cell count (cells/ml) | <$10^3$ | <$10^3$ |
| | Mold cell count (cells/ml) | <10 | <10 |
| | Yeast-like fungus cell count (cells/ml) | <10 | <10 |
| | Unpleasant odor | A | A |
| Ex. 8 | pH | 9.1 | 9.0 |
| | Viable cell count (cells/ml) | <$10^3$ | <$10^3$ |
| | Mold cell count (cells/ml) | <10 | <10 |
| | Yeast-like fungus cell count (cells/ml) | <10 | <10 |
| | Unpleasant odor | A | A |
| Ex. 9 | pH | 8.9 | 8.8 |
| | Viable cell count (cells/ml) | <$10^3$ | $4 \times 10^3$ |
| | Mold cell count (cells/ml) | <10 | <10 |
| | Yeast-like fungus cell count (cells/ml) | <10 | <10 |
| | Unpleasant odor | A | A |
| Comp. Ex. 1 | pH | 8.6 | 8.5 |
| | Viable cell count (cells/ml) | $3 \times 10^3$ | $4 \times 10^4$ |
| | Mold cell count (cells/ml) | $2 \times 10^2$ | $4 \times 10^3$ |
| | Yeast-like fungus cell count (cells/ml) | $4 \times 10^3$ | $5 \times 10^4$ |
| | Unpleasant odor | C | C |
| Comp. Ex. 2 | pH | 8.8 | 8.6 |
| | Viable cell count (cells/ml) | $8 \times 10^3$ | $3 \times 10^5$ |
| | Mold cell count (cells/ml) | $4 \times 10^2$ | $7 \times 10^3$ |
| | Yeast-like fungus cell count (cells/ml) | $6 \times 10^3$ | $8 \times 10^4$ |
| | Unpleasant odor | C | C |
| Comp. Ex. 3 | pH | 8.1 | 7.6 |
| | Viable cell count (cells/ml) | $7 \times 10^6$ | $8 \times 10^7$ |
| | Mold cell count (cells/ml) | $6 \times 10^2$ | $4 \times 10^4$ |
| | Yeast-like fungus cell count (cells/ml) | $4 \times 10^4$ | $8 \times 10^5$ |
| | Unpleasant odor | C | C |

TABLE 4-1

| Sample | Item tested | Days passed 0 | Days passed 3 | Days passed 7 |
|---|---|---|---|---|
| Ex. 10 | pH | 9.6 | 9.5 | 9.5 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |
| | Unpleasant odor | A | A | A |
| Ex. 11 | pH | 9.7 | 9.6 | 9.5 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |
| | Unpleasant odor | A | A | A |
| Ex. 12 | pH | 9.7 | 9.6 | 9.5 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |
| | Unpleasant odor | A | A | A |
| Ex. 13 | pH | 9.5 | 9.4 | 9.3 |
| | Viable cell count (cells/ml) | 0 | <$10^3$ | <$10^3$ |
| | Mold cell count (cells/ml) | 0 | <10 | <10 |
| | Yeast-like fungus cell count (cells/ml) | 0 | <10 | <10 |

TABLE 4-1-continued

| Sample | Item tested | Days passed 0 | 3 | 7 |
|---|---|---|---|---|
| | Unpleasant odor | A | A | A |
| Ex. 14 | pH | 9.6 | 9.5 | 9.5 |
| | Viable cell count (cells/ml) | 0 | $<10^3$ | $<10^3$ |
| | Mold cell count (cells/ml) | 0 | $<10$ | $<10$ |
| | Yeast-like fungus cell count (cells/ml) | 0 | $<10$ | $<10$ |
| | Unpleasant odor | A | A | A |
| Ex. 15 | pH | 9.4 | 9.4 | 9.3 |
| | Viable cell count (cells/ml) | 0 | $<10^3$ | $<10^3$ |
| | Mold cell count (cells/ml) | 0 | $<10$ | $<10$ |
| | Yeast-like fungus cell count (cells/ml) | 0 | $<10$ | $<10$ |
| | Unpleasant odor | A | A | A |
| Ex. 16 | pH | 9.5 | 9.4 | 9.4 |
| | Viable cell count (cells/ml) | 0 | $<10^3$ | $<10^3$ |
| | Mold cell count (cells/ml) | 0 | $<10$ | $<10$ |
| | Yeast-like fungus cell count (cells/ml) | 0 | $<10$ | $<10$ |
| | Unpleasant odor | A | A | A |
| Comp. Ex. 4 | pH | 9.5 | 9.4 | 9.4 |
| | Viable cell count (cells/ml) | 0 | $<10^3$ | $<10^3$ |
| | Mold cell count (cells/ml) | 0 | $<10$ | $<10$ |
| | Yeast-like fungus cell count (cells/ml) | 0 | $1 \times 10^2$ | $2 \times 10^3$ |
| | Unpleasant odor | A | A | A |
| Comp. Ex. 5 | pH | 9.5 | 9.4 | 9.3 |
| | Viable cell count (cells/ml) | 0 | $<10^3$ | $<10^3$ |
| | Mold cell count (cells/ml) | 0 | $<10$ | 20 |
| | Yeast-like fungus cell count (cells/ml) | 0 | $1 \times 10^2$ | $3 \times 10^3$ |
| | Unpleasant odor | A | A | C |
| Comp. Ex. 6 | pH | 9.4 | 9.2 | 8.9 |
| | Viable cell count (cells/ml) | 0 | $4 \times 10^3$ | $7 \times 10^4$ |
| | Mold cell count (cells/ml) | 0 | $<10$ | 60 |
| | Yeast-like fungus cell count (cells/ml) | 0 | $3 \times 10^2$ | $6 \times 10^3$ |
| | Unpleasant odor | A | B | C |

TABLE 4-2

| Sample | Item tested | Days passed 14 | 21 |
|---|---|---|---|
| Ex. 10 | pH | 9.4 | 9.3 |
| | Viable cell count (cells/ml) | $<10^3$ | $<10^3$ |
| | Mold cell count (cells/ml) | $<10$ | $<10$ |
| | Yeast-like fungus cell count (cells/ml) | $<10$ | $<10$ |
| | Unpleasant odor | A | A |
| Ex. 11 | pH | 9.4 | 9.4 |
| | Viable cell count (cells/ml) | $<10^3$ | $3 \times 10^3$ |
| | Mold cell count (cells/ml) | $<10$ | $<10$ |
| | Yeast-like fungus cell count (cells/ml) | $<10$ | $<10$ |
| | Unpleasant odor | A | A |
| Ex. 12 | pH | 9.5 | 9.4 |
| | Viable cell count (cells/ml) | $<10^3$ | $<10^3$ |
| | Mold cell count (cells/ml) | $<10$ | $<10$ |
| | Yeast-like fungus cell count (cells/ml) | $<10$ | $<10$ |
| | Unpleasant odor | A | A |
| Ex. 13 | pH | 9.2 | 9.2 |
| | Viable cell count (cells/ml) | $<10^3$ | $<10^3$ |
| | Mold cell count (cells/ml) | $<10$ | $<10$ |
| | Yeast-like fungus cell count (cells/ml) | $<10$ | $<10$ |
| | Unpleasant odor | A | A |
| Ex. 14 | pH | 9.4 | 9.4 |
| | Viable cell count (cells/ml) | $<10^3$ | $<10^3$ |
| | Mold cell count (cells/ml) | $<10$ | $<10$ |
| | Yeast-like fungus cell count (cells/ml) | $<10$ | $<10$ |
| | Unpleasant odor | A | A |
| Ex. 15 | pH | 9.2 | 9.2 |
| | Viable cell count (cells/ml) | $<10^3$ | $<10^3$ |
| | Mold cell count (cells/ml) | $<10$ | $<10$ |
| | Yeast-like fungus cell count (cells/ml) | $<10$ | $<10$ |
| | Unpleasant odor | A | A |
| Ex. 16 | pH | 9.3 | 9.2 |
| | Viable cell count (cells/ml) | $<10^3$ | $<10^3$ |
| | Mold cell count (cells/ml) | $<10$ | $<10$ |
| | Yeast-like fungus cell count (cells/ml) | $<10$ | $<10$ |
| | Unpleasant odor | A | A |
| Comp. Ex. 4 | pH | 9.3 | 9.2 |
| | Viable cell count (cells/ml) | $<10^3$ | $<10^3$ |
| | Mold cell count (cells/ml) | $<10$ | $<10$ |
| | Yeast-like fungus cell count (cells/ml) | $6 \times 10^3$ | $4 \times 10^4$ |
| | Unpleasant odor | B | C |
| Comp. Ex. 5 | pH | 9.2 | 9.1 |
| | Viable cell count (cells/ml) | $3 \times 10^4$ | $9 \times 10^6$ |
| | Mold cell count (cells/ml) | $1 \times 10^2$ | $3 \times 10^2$ |
| | Yeast-like fungus cell count (cells/ml) | $4 \times 10^4$ | $6 \times 10^4$ |
| | Unpleasant odor | C | C |
| Comp. Ex. 6 | pH | 8.6 | 8.1 |
| | Viable cell count (cells/ml) | $3 \times 10^6$ | $6 \times 10^7$ |
| | Mold cell count (cells/ml) | $3 \times 10^2$ | $3 \times 10^5$ |
| | Yeast-like fungus cell count (cells/ml) | $2 \times 10^4$ | $7 \times 10^5$ |
| | Unpleasant odor | C | C |

(Evaluation Results)

From Table 3 and Table 4, the following findings have been obtained.

(1) pH

The samples of the examples exhibited a very small pH drop, 0.4 at the maximum, even after the elapsed time of 21 days. In contrast, the samples of the comparative examples underwent a pH drop as great as 1.4 at the maximum.

(2) Viable cell counts and fungus cell counts

In the case of the samples of the examples, the viable cell count was as great as $4 \times 10^3$ cells/ml at the maximum even after the elapsed time of 21 days. The samples of the comparative examples included those showing a substantial increase in viable cell count up to $8 \times 10^7$ at the maximum.

Further, the fungi cell count was smaller than 10 cells/ml in each of the samples of the examples even after the elapsed time of 21 days. However, the fungi cell counts of most of the samples of the comparative examples increased significantly, including samples in which the fungi cell counts increased to as great as $8 \times 10^5$ cells/ml.

Incidentally, the sample of Comparative Example 4 showed the good results that its mold cell count was still smaller than 10 cells/ml even after the elapsed time of 21 days. However, the yeast-like fungus count increased considerably to $4 \times 10^4$ cells/ml. It is therefore clear that the sample had weak antibacterial activities against yeast-like fungi.

(3) Unpleasant odor

None of the samples of the examples developed any noticeable putrefactive odor even after the elapsed time of 21 days. In contrast, the samples of all the comparative examples gave putrefactive odor after the elapsed time of 21 days.

It is therefore clearly envisaged that the water-soluble cutting fluids of the invention examples are far superior in the resistance to deterioration by microorganisms to the conventional cutting fluids of the comparative examples.

(Application Examples)

To further demonstrate the practical effectiveness of the water-soluble cutting fluids according to the present invention, two manufacturing lines in which severe deterioration by microorganisms had taken place for many years were chosen. The water-soluble cutting fluids of Example 1 and Comparative Example 1 were tested by applying them to the actual machines in the manufacturing lines.

| Machined material | "ADC-12", sintered alloy |
|---|---|
| Machining work | Boring (drill, reamer, tap) |
| Capacity of tank for cutting fluid | 40,000 liters |
| Dilution of cutting fluid | 30 times |
| Amount of stock solution replenished | 1,200 l/month |
| Test period | 6 months. The cutting fluid of the comparative example was tested first, followed by the testing of the cutting fluid of the example. |

The results are shown in Table 5.

TABLE 5-1

| Fluid | Item tested | Time passed (month) | | | |
|---|---|---|---|---|---|
| | | 0 | 1 | 2 | 3 |
| Ex. 1 | pH | 9.2 | 9.6 | 9.5 | 9.5 |
| | Viable cell count (cells/ml) | 0 | $<10^3$ | $<10^3$ | $<10^3$ |
| | Mold cell count (cells/ml) | 0 | $<10$ | $<10$ | $<10$ |
| | Unpleasant odor | A | A | A | A |
| Comp. Ex. 1 | pH | 9.0 | 8.8 | 8.7 | 8.6 |
| | Viable cell count (cells/ml) | 0 | $<10^3$ | $4 \times 10^4$ | $2 \times 10^5$ |
| | Mold cell count (cells/ml) | 0 | 30 | $2 \times 10^2$ | $6 \times 10^3$ |
| | Unpleasant odor | A | A | B | B |

TABLE 5-2

| Fluid | Item tested | Time passed (month) | | |
|---|---|---|---|---|
| | | 4 | 5 | 6 |
| Ex. 1 | pH | 9.2 | 9.1 | 9.2 |
| | Viable cell count (cells/ml) | $<10^3$ | $<10^3$ | $<10^3$ |
| | Mold cell count (cells/ml) | $<10$ | $<10$ | $<10$ |
| | Unpleasant odor | A | A | A |
| Comp. Ex. 1 | pH | 8.6 | 8.5 | 8.6 |
| | Viable cell count (cells/ml) | $3 \times 10^5$ | $1 \times 10^6$ | $1 \times 10^6$ |
| | Mold cell count ml) | $2 \times 10^4$ | $3 \times 10^6$ | $5 \times 10^4$ |
| | Unpleasant odor | C | C | C |

(Note) The measurement of each item was conducted in a similar manner to the above-described performance evaluation test.
(ii) Automobile transmission case machining line:
Machined material: "ADC-12", sintered alloy
Machining work: Boring (drill, reamer, tap)
Capacity of tank for cutting fluid: 50,000 liters
Dilution of cutting fluid: 50 times
Amount of stock solution replenished: 1,000 l/month
Test period: 6 months. The cutting fluid of Comparative Example 5 was tested first, followed by the testing of the cutting fluid of Example 11.

The results are shown in Table 6.

TABLE 6-1

| Fluid | Item tested | Time passed (month) | | |
|---|---|---|---|---|
| | | 0 | 1 | 2 |
| Ex. 1 | pH | 9.7 | 9.7 | 9.6 |
| | Viable cell count (cells/ml) | 0 | $<10^3$ | $<10^3$ |
| | Mold cell count (cells/ml) | 0 | $<10$ | $<10$ |
| | Unpleasant odor | A | A | A |
| Comp. Ex. 5 | pH | 9.5 | 9.1 | 8.6 |
| | Viable cell count (cells/ml) | 0 | $<10^3$ | $2 \times 10^3$ |
| | Mold cell count (cells/ml) | 0 | 15 | $5 \times 10^2$ |
| | Unpleasant odor | A | A | C |

TABLE 6-2

| Fluid | Item tested | Time passed (month) | | | |
|---|---|---|---|---|---|
| | | 3 | 4 | 5 | 6 |
| Ex. 1 | pH | 9.6 | 9.5 | 9.6 | 9.6 |
| | Viable cell count (cells/ml) | $<10^3$ | $<10^3$ | $<10^3$ | $<10^3$ |
| | Mold cell count (cells/ml) | $<10$ | $<10$ | $<10$ | $<10$ |
| | Unpleasant odor | A | A | A | A |
| Comp. Ex. 5 | pH | 8.7 | 8.6 | 8.5 | 8.6 |
| | Viable cell count (cells/ml) | $6 \times 10^5$ | $1 \times 10^6$ | $1 \times 10^6$ | $2 \times 10^6$ |
| | Mold cell count (cells/) ml) | $3 \times 10^4$ | $2 \times 10^4$ | $3 \times 10^4$ | $5 \times 10^4$ |
| | Unpleasant odor | A | A | B | B |

(Note) The measurement of each item was conducted in a similar manner to the above-described performance evaluation test.

From Tables 5 and 6, it has been confirmed that the water-soluble cutting fluids according to the present invention have excellent resistance to deterioration by microorganisms even in actual applications, compared to conventional water-soluble cutting fluids.

What is claimed is:

1. In an antimicrobial water-soluble cutting fluid comprising a mineral oil and/or fatty oil, an extreme-pressure additive and a surfactant, the improvement wherein said fluid further comprises an amine or amine derivative represented by the following formula (I):

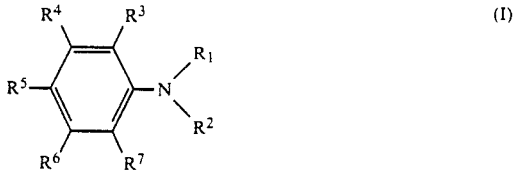

(I)

or by the following (II):

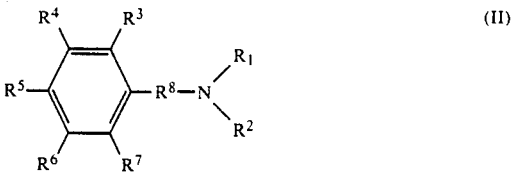

(II)

wherein $R^1$ through $R^7$ individually mean a hydrogen atom, a substituted or unsubstituted alkyl, alkenyl, cycloalkyl, alkylaryl, aralkyl, aryl, hydroxyalkyl or alkoxyl group, or a nitrogen-containing heterocyclic group having up to 10 carbon atoms, $R^1$ and $R^2$ may be coupled together into a nitrogen-containing heterocyclic group along with the nitrogen atom to which $R^1$ and $R^2$ are bonded, or $R^3$ through $R^7$ individually mean a hydroxyl, amino, substituted amino, aminocarbonyl or aliphatic acyl group, and $R^8$ denotes an alkylene group having 1-4 carbon atoms.

2. The fluid of claim 1, wherein the amine or amine derivative is at least one anilinoamine represented by the formula (I), which is selected from aniline, o-anisidine, m-anisidine, p-anisidine, 4-methoxy-2-methylaniline, amidol, 4-anilino-m-phenylenediamine, 4-cyclohexylaniline, 2-anilinoethanol, 2-anilinodiethanol, anilinodi-2-propanol, m-anilinophenol, 2-aminoacetophenone, 4-aminobenzamide, 3-anilinopropionitrile and N-phenyl-p-phenylenediamine.

3. The fluid of claim 1, wherein the amine or amine derivative is at least one aralkylamine represented by the formula (II), which is selected from benzylamine, dibenzylamine, o-methoxydibenzylamine, m-methoxydibenzylamine, p-methoxydibenzylamine, N,N-dimethylbenzylamine, N,N-diethylbenzylamine, N-methylbenzylamine, N-phenylbenzylamine, N-phenyl-N-ethylbenzylamine, N-(2-hydroxyethyl)benzylamine, N-(t-butyl)benzylamine, p-benzylaminophenol, 2-benzylaminopyridine, 1-benzyl-3-aminopyrrolidine, N-benzyl-3-aminopyrrolidine, N-benzyll-4-piperidone, 2-phenylethylamine, 2-phenylbutylamine, d,l-α-methylbenzylamine, N,N-dimethyl-d-α-methylbenzylamine, 4-phenylbutylamine, 2-phenyl-t-butylamine and m-xylenediamine.

4. A coolant obtained by diluting with water a water-soluble cutting fluid comprising as essential components a mineral oil and/or fatty oil, an extreme-pressure additive and a surfactant, the improvement wherein said coolant further comprises 0.001-1 wt. % of an amine or amine derivative represented by the following formula (I):

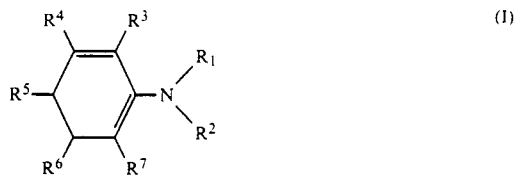

or by the following (II):

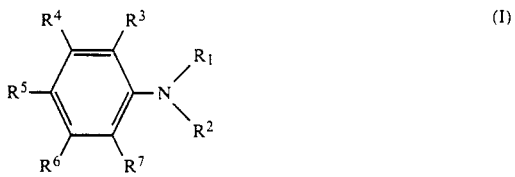

wherein $R^1$ through $R^7$ individually mean a hydrogen atom, a substituted or unsubstituted alkyl, alkenyl, cycloalkyl, alkylaryl, aralkyl, aryl, hydroxyalkyl or alkoxy group, or a nitrogen-containing heterocyclic group having up to 10 carbon atoms, $R^1$ and $R^2$ may be combined together into a nitrogen-containing heterocyclic group along with the nitrogen atom to which $R^1$ and $R^2$ are bonded, or $R^3$ through $R^7$ individually mean a hydroxyl, amino, substituted amino, aminocarbonyl or aliphatic acyl group, and $R^8$ denotes an alkylene group having 1-4 carbon atoms.

* * * * *